United States Patent [19]

McGuirk

[11] Patent Number: 5,385,913
[45] Date of Patent: Jan. 31, 1995

[54] 1,4-DIHYDRO-4-OXO-3-QUINOLINE DERIVATIVES AS SELECTIVELY TOXIC MAMMALIAN ANTIBACTERIAL AGENTS

[75] Inventor: Paul R. McGuirk, Ledyard, Conn.
[73] Assignee: Pfizer Inc., New York, N.Y.
[21] Appl. No.: 842,205
[22] PCT Filed: Oct. 6, 1989
[86] PCT No.: PCT/US89/04438
§ 371 Date: Mar. 26, 1992
§ 102(e) Date: Mar. 26, 1992
[87] PCT Pub. No.: WO91/04972
PCT Pub. Date: Apr. 18, 1991
[51] Int. Cl.⁶ .................... A61K 31/47; C07D 401/10
[52] U.S. Cl. .................... 514/312; 546/156; 560/170; 560/174; 544/349
[58] Field of Search .......... 546/156; 514/312; 544/349

[56] References Cited

U.S. PATENT DOCUMENTS

| | | | |
|---|---|---|---|
| 3,947,445 | 3/1976 | Henry et al. | 548/453 |
| 4,382,892 | 5/1983 | Hayakawa et al. | 540/575 |
| 4,416,884 | 1/1983 | Ishikawa et al. | 514/254 |
| 4,571,396 | 2/1986 | Hutt et al. | 514/249 |
| 4,775,668 | 10/1988 | Jefson et al. | 514/183 |
| 4,851,418 | 7/1989 | Sanchez | 514/300 |
| 4,861,779 | 8/1989 | Jefson et al. | 514/249 |
| 4,973,590 | 11/1990 | Preiss et al. | 514/254 |
| 4,980,470 | 12/1990 | Masuzawa et al. | 544/363 |
| 4,997,943 | 5/1991 | Iwata et al. | 544/363 |

FOREIGN PATENT DOCUMENTS

| | | |
|---|---|---|
| 0159174 | 10/1985 | European Pat. Off. . |
| 0230274 | 7/1987 | European Pat. Off. . |
| 0230295 | 7/1987 | European Pat. Off. . |
| 0230295A2 | 7/1987 | European Pat. Off. . |
| 0241206 | 10/1987 | European Pat. Off. . |
| 274033A1 | 7/1988 | European Pat. Off. . |
| 284935A1 | 10/1988 | European Pat. Off. . |
| 304087A2 | 2/1989 | European Pat. Off. . |

OTHER PUBLICATIONS

Anonymous Research Disclosure No. 28737 "Rhinologic Containing Gyrase Retarder" (Mar. 1988).
Barrett, John F. et al. "Use of In Vitro Topiosomerase II Assays for Studying Quinolone Antibacterial Agents", *Antimicrobial Agents and Chemotherapy*, Oct. 1989, pp. 1697–1703.
Barrett et al., "Use of In Vitro Topoisomerase II Assays for Studying Quinolone Antibacterial Agents," *Antimicrobial Agents and Chemotherapy*, 33, No. 10, pp. 1697–1703 (1989).
Derwent Abstract –Anonymous Research Disclosure No. 88-103314/15 "Medical Use of Gyrase Inhibitors For Local Treatment of Nasal Infections" (1988).

Primary Examiner—Emily Bernhardt
Attorney, Agent, or Firm—Peter C. Richardson; Paul H. Ginsburg; Philip C. Strassburger

[57] ABSTRACT

Compounds of the formula

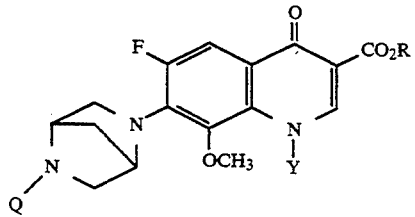

and the pharmaceutically acceptable salts thereof, wherein Q, X and R are as defined below. The compounds of formula I are broad spectrum mammalian antibacterial agents and exhibit favorable selectivity against procaryotic cells.

3 Claims, No Drawings

1,4-DIHYDRO-4-OXO-3-QUINOLINE DERIVATIVES AS SELECTIVELY TOXIC MAMMALIAN ANTIBACTERIAL AGENTS

BACKGROUND OF THE INVENTION

The present invention relates to new 1,4-dihydro-4-oxo-3-quinoline derivatives that are antibacterial agents suitable for the treatment of bacterial and mycoplasma infections in mammals, including humans. The compounds of the invention exhibit unexpectedly favorable selectivity against procaryotic cells, as measured by their activity against procaryotic DNA gyrase versus mammalian topoisomerase II.

U.S. Pat. Nos. 4,775,668 and 4,861,779 refer to antibacterial compounds having the formula

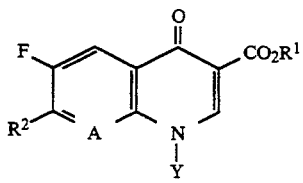

wherein $R^1$ is hydrogen, a pharmaceutically acceptable cation, or alkyl; A is CH, CF, CCl or N; Y is alkyl, haloalkyl, cyclopropyl, vinyl, methoxy, N-methylamino, p-flurophenyl, p-hydroxyphenyl or p-aminophenyl; or A is carbon and is taken together with Y and the carbon and nitrogen to which A and Y are attached to form a five to seven membered ring which is optionally substituted; and $R^2$ is a bridged-diazabicycloalkyl group.

Derwent anonymous research disclosure no. 88-103269/15 refers to compounds of the formula

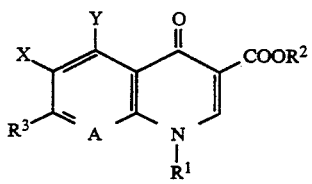

wherein $R^1$ is ($C_1$-$C_3$)alkyl, cyclopropyl, vinyl, hydroxyethyl, fluoroethyl, methoxy, amino, methylamino, dimethylamino, ethylamino, phenyl, 4-fluorophenyl or 2,4-difluorophenyl; $R^2$ is hydrogen, ($C_1$-$C_4$)alkyl or 5-methyl-2-oxo-1,3-dioxol-4-ylmethyl; $R^3$ is methyl or one of eleven cyclic amino groups wherein one of said eleven cyclic amino groups is

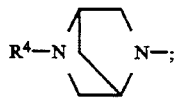

$R^4$ is hydrogen, ($C_1$-$C_4$) alkyl, hydroxyethyl, allyl, propargyl, $CH_2COCH_3$, phenacyl, CHO, $SCFCl_2$, $SO_2CFCl_2$, SCOOMe, benzyl, 4-aminobenzyl or 5-methyl-2-oxo-1,3-dioxo-4-ylmethyl; $R^5$ is hydrogen or methyl; $R^6$ is hydrogen, ($C_1$-$C_4$) alkyl, phenyl or $CH_2OCH_2Ph$; $R^7$ is hydrogen, amino, methylamino, ethylamino, aminomethyl, methylaminomethyl, ethylaminomethyl, dimethylaminomethyl, hydroxy or hydroxymethyl; $R^8$ is methyl, ethyl or chloro; X is fluyoro, chloro or nitro; Y is hydrogen, fluoro or amino; A is nitrogen or $CR^9$; and $R^9$ is hydrogen, alkoxy, ($C_1$-$C_3$)alkylthio, halogen, methyl or nitro; or $R^1$ and $R^9$ are $OCH_2CH(Me)$, $SCH_2CH(Me)$, $COCH_2CH(Me)$ or $CH_2CH_2CH(Me)$. This broad generic disclosure includes several compounds of the present invention but does not teach or suggest their surprising and favorable selectivity as antibacterial agents against procaryotic versus eucaryotic cells.

SUMMARY OF THE INVENTION

The present invention relates to compounds of the formula

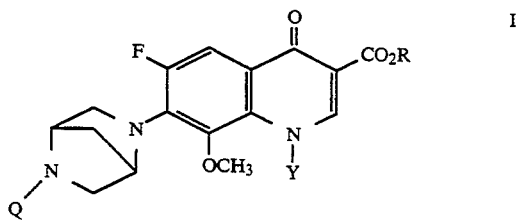

wherein Q is methyl, ethyl, hydroxyethyl or hydrogen; R is hydrogen, ($C_1$-$C_3$) alkyl, benzyl, ($C_1$-$C_3$) alkanoyloxymethyl, ($C_1$-$C_3$) alkanoyloxyethyl, benzoyloxymethyl, benzoyloxyethyl, or 5-[($C_1$-$C_3$)alkyl]-2-oxo-1,3-dioxolen-4-ylmethyl; and Y is cyclopropyl or substituted cyclopropyl, wherein said substituted cyclopropyl is substituted with one to three substituents independently selected from the group consisting of ($C_1$-$C_3$) alkyl, halo hydroxy, or ($C_1$-$C_3$) alkoxy;

and the pharmaceutically acceptable salts and hydrates of such compounds.

As used herein, unless indicated otherwise, "halo" includes fluoro, chloro, bromo and iodo.

Examples of pharmaceutically acceptable salts of the compounds of formula I are the acid addition salts of acetic, lactic, succinic, maleic, tartaric, citric, gluconic, ascorbic, benzoic, methanesulfonic, cinnamic, fumaric, phosphoric, hydrochloric, hydrobromic, hydroiodic, and sulfonic acids, and the cationic salts of alkali metals such as sodium or potassium, alkaline earth metals such as magnesium or calcium, ammonium, and organic amines such as diethanolamine and N-methylglucamine.

The term "pharmaceutically acceptable salts and hydrates", as used herein, includes pharmaceutically acceptable salts, hydrates, pharmaceutically acceptable salts of hydrates, and hydrates of such salts.

The present invention also relates to a pharmaceutical composition comprising an antibacterially effective amount of a compound of the formula I, or a pharmaceutically acceptable salt thereof, and a pharmaceutically acceptable carrier.

The present invention also relates to a method of treating a mammal, including a human, having a bacterial disease, which comprises administering to the mammal an antibacterially effective amount of a compound of the formula I, or a pharmaceutically acceptable salt thereof.

Compounds of the formula I wherein R is ($C_1$-$C_3$) alkyl, benzyl, ($C_1$-$C_3$) alkanoyloxymethyl, ($C_1$-$C_3$) alkanoyloxyethyl, ($C_1$-$C_3$) benzoyloxymethyl, ($C_1$-$C_3$) benzoyloxyethyl or 5-[($C_1$-$C_3$)alkyl]-2-oxo-1,3-dioxolen-4-ylmethyl, are prodrugs of compounds of the formula I wherein R is hydrogen.

The compounds of the formula I may have chiral centers and may exist in several stereoisomeric forms. This invention includes all stereoisomers of the compounds of formula I, and mixtures thereof.

Preferred compounds of the invention are 1-cyclopropyl-6-fluoro-8-methoxy-7-(1S, 4S)-5-methyl-2,5-diazabicyclo[2.2.1]hept-2-yl -1,4-dihydro-4-oxo-3-quinoline carboxylic acid and the pharmaceutically acceptable salts and hydrates thereof.

DETAILED DESCRIPTION OF THE INVENTION

Compounds of the formula I may be prepared as illustrated in the following reaction scheme.

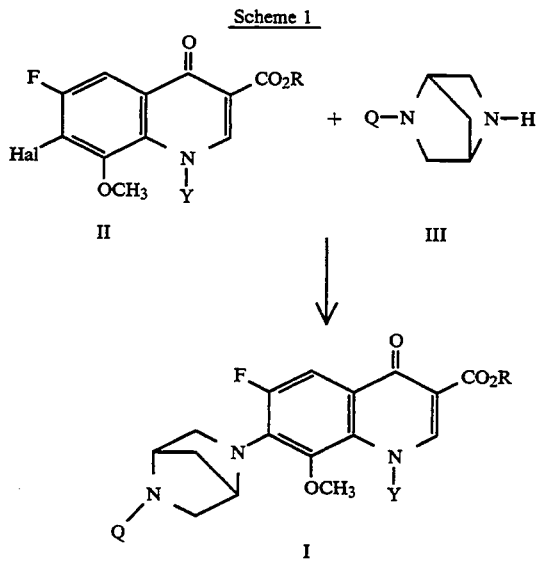

Referring to the above reaction scheme, compounds of the formula I, wherein Q is hydrogen and R and Y are as defined above, may be prepared by reacting a compound of the formula II, wherein R and Y are as defined above and Hal is chloro, bromo, fluoro or iodo, with a compound of the formula III.

The reaction may be performed in the absence of a solvent or in the presence of a polar, reaction inert solvent such as acetonitrile, tetrahydrofuran, ethanol, chloroform, dimethylformamide, pyridine, or water, or mixtures thereof. The reaction is preferably carried out in the presence of a base such as an alkali metal or alkaline earth metal carbonate or bicarbonate, or a secondary or tertiary amine such as triethylamine, pyridine or picoline. The preferred reaction temperature is from about 60° to about 100° C., but temperatures from about 10° to about 150° C. are generally suitable.

The starting materials of formula II are known in the art, e.g. as disclosed in European Patent Application 0230295A2.

Compounds of the formula III, wherein Q is hydrogen, may be made as described in U.S. Pat. No. 3,947,445 and in J. Org. Chem., 31, 1059 (1966).

Compounds of the formula I wherein Q is methyl may be prepared from the corresponding compounds of the formula I wherein Q is hydrogen by conventional methylation procedurs. For example, one standard methylation procedure known in the art involves the use of formic acid and paraformaldehyde. According to this procedure, a mixture of an alkali or alkaline earth metal formate (preferably sodium formate), formic acid (preferably 87% formic acid), formalin (preferably 37% formalin), and a compound of the formula I wherein Q is hydrogen are reacted to yield a compound of the formula I wherein Q is methyl. The reaction is typically carried out by stirring the reactants for approximately 0.5 to 24 hours, preferably about 2 hours, at a temperature of from about 80° to about 150° C., preferably from 100° to 120° C. The compounds of formula I so produced can be isolated by conventional purification techniques.

Compounds of the formula I wherein Q is ethyl or hydroxyethyl may be prepared by reacting a compound of the formula I wherein Q is hydrogen with, respectively, ethyl iodide or 2-bromoethanol. This reaction is generally carried out in a reaction inert solvent such as tetrahydrofuran (THF) or dimethylformamide (DMF), and in the presence of an organic base such as triethylamine, at a temperature of from about 50° to 150° C., preferably about 100° C., for approximately 24 hours. The compound of formula I so produced can be isolated by conventional purification techniques.

In each of the reactions described above, pressure is not critical. Pressures from about 0.5 to about 3 atmospheres are generally suitable, and ambient pressure is preferred as a matter of convenience.

The pharmaceutically acceptable acid addition salts of compounds the formula I may be prepared in a conventional manner by treating a solution or suspension of the free base of the formula I with about one chemical equivalent of a pharmaceutically acceptable acid. Conventional concentration and recrystallization techniques are employed in isolating the salts.

The pharmaceutically acceptable cationic salts of compounds of the formula I may be prepared by conventional methods from the corresponding acids, e.g. by reaction with about one equimolar amount of a base.

The novel compounds of the formula I and the pharmaceutically acceptable acid addition salts thereof are useful in the treatment of bacterial infections of broad spectrum, particularly in the treatment of gram-positive bacterial infections.

The compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1 to about 50 mg/kg/day, preferably about 0.2 to about 10 mg/kg/day given in a single daily dose or up to 4 divided doses.

The compounds of the invention can be administered to humans for the treatment of bacterial diseases by either the oral or parenteral routes and may be administered orally at dosage levels of about 0.1 to about 500 mg/kg, advantageously about 0.5 to about 50 mg/kg/day given in a single dose or up to 4 divided doses. For intramuscular or intravenous administration, dosage levels are about 0.1 to about 200 mg/kg/day, preferably about 0.5 to about 50 mg/kg/day. While intramuscularly administration may be a single dose or up to 4 divided doses, intravenous administration can include a continuous drip. Variations will necessarily occur depending on the weight and condition of the subject being treated and the particular route of administration chosen as will be known to those skilled in the art.

The antibacterial activity of the compounds of the present invention may be determined by testing according to the Steer's replicator techniques, which is a standard in vitro bacterial testing method described by E. Steers et al., *Antibiotics and Chemotherapy*, 9, 307 (1959). The selective antibacterial activity of the compounds of the formula I against procaryotic versus eucaryotic cells may be determined by comparing their activity against procaryotic DNA-gyrase versus mammalian topoisomerase II according to the procedure of Barrett et al., *Antimicrobial Agents and Chemotherapy*, 33 (10) (October, 1989).

The following examples serve to illustrate but not limit the present invention.

EXAMPLE 1 a. Ethyl 3-methoxy-2,4,5-trifluorobenzoylacetate

Dianion of monoethylamalonate: To a solution of monoethylmalonic acid (9.8 g, 73 mmol) in anhydrous tetrahydrofuran (350 mL) at −78° C. was added n-butyllithium (50 mL, 80 mmol, 1.6 M, 1.1 equiv). The reaction temperature was then raised to −5° C. and additional n-butyllithium was added (50 mL, 80 mmol, 1.6 M, 1.1 equiv.) dropwise. The reaction mixture was allowed to stir for an additional hour at −5° C. and was then cooled to 78° C.

Addition of acid chloride: 3-Methoxy-2,4,5-trifluorobenzoyl chloride (6.38 g, 24 mmol), prepared from 3-methoxy-2,4,5-trifluorobenzoic acid (5.0 g, 24 mmol) and excess thionyl chloride at reflux for 2 hours followed by removal of excess thionyl chloride in vacuo, was added dropwise as a solution in anhydrous tetrahydrofuran (50 mL) to the dianion of monoethylmalonate at −78° C. The reaction mixture was allowed to warm to room temperature for 2 hours and was quenched by pouring into 1N hydrochloric acid. The aqueous layer was extracted with diethyl ether (3×150 mL) and the combined organic layers were washed with saturated aqueous sodium bicarbonate and water, dried over anhydrous magnesium sulfate, filtered and concentrated in vacuo to afford 5.15 g, 76% yield of a white solid after recrystallization from hexanes, m.p. 42°–44° C.

Anal.: Calcd. for $C_{12}H_{11}F_3O_4$: C, 52.20; H, 3.90. Found: C, 52.18; H, 3.85.

MS (low resolution) M+ =276.

b. Ethyl 2-(3-methoxy-2,4,5-triflurobenzoyl)-3-ethoxyacrylate

A mixture of ethyl-3-methoxy-2,4,5-trifluorobenzoylacetate (500 mg, 1.8 mmol), ethyl orthoformate (0.45 mL, 2.72 mmol) and acetic anhydride (460 mg, 4.5 mmol, 2.5 eq) was stirred at 110° C. for 12 hours and the excess reagents were removed by distillation under high vacuum (0.1 mmHg) to give 590 mg of a yellow-orange oil. This material was used directly in the next step without further purification or characterization.

c. Ethyl 2-(3-methoxy-2,4,5-trifluorobenzoyl)-3-cyclopropylaminoacrylate

To a solution of ethyl 2-(3-methoxy-2,4,5-triflurobenzoyl)-3-ethoxyacrylate (590 mg, 1.8 mmol) in methylene chloride (15 mL) at 0° C. was added a solution of cyclopropylamine (114 mg, 1.98 mmol, 1.2 equiv) in methylene chloride (5 mL). The reaction mixture was warmed to room temperature and allowed to stir for 2 hours. The solvent was removed in vacuo and the crude concentrate was purified by flash chromatography on silica gel (methylene chloride/ethyl acetate 50:1 v/v) to provide 438 mg, 62% yield over two steps, of a viscous yellow oil.

d. Ethyl 8-methoxy-1-cyclopropyl-6,7-difluoro-1,4-dihydro-4-oxo-3-quinolinecarboxylate To a solution of ethyl 2-(3-methoxy-2,4,5-trifluorobenzoyl)-3-cyclopropylaminoacrylate (440 mg, 1.29 mmol) in anhydrous tetrahydrofuran (15 mL) at 0° C. was added sodium hydride (62 mg, 1.5 mmol, 1.1 equiv, 60% in mineral oil). The reaction mixture was allowed to stir at 50° C. for 12 hours. The mixture was cooled to room temperature and filtered. The mother liquor was concentrated and a white precipitate formed. The material was collected by suction filtration and air-dried to give 312 mg, 75% yield of a pure white solid, m.p. 178°–181° C.

e. 1-Cyclopropyl-6,7-difluoro-8-methoxy-1,4-dihydro-4-oxo-3-quinolinecarboxylic acid A mixture of ethyl-1-cyclopropyl-6,7-difluoro-8-methoxy-1,4-dihydro-4-oxo-3-quinoline carboxylic acid (500 mg, 1.55 mmol), glacial acetic acid (5 mL), and 1N hydrochloric acid (1 mL) was allowed to reflux for 2 hours and was poured into ice water. The resulting precipitate was collected by suction filtration and washed with distilled water and diethyl ether to give 420 mg, 91% yield of a white solid, m.p. 187°–189° C.

f. 1-Cyclopropyl-6-fluoro-8-methoxy-7-[(1S:4S)-5-methyl-2,5-diazabicyclo[2.2.1]hept-2-yl]-1,4-dihydro-4-oxo-3-quinolinecarboxylic acid A mixture of 1-cyclopropyl-6,7-difluoro-8-methoxy-1,4-dihydro-4-oxo-3-quinolinecarboxylic acid (400 mg, 1.4 mmol), (1S:4S)-2-methyl-2,5-diazabicyclo[2.2.1]heptane dihydrochloride (300 mg, 1.63 mmol, 1.2 equiv) and 1,8-diazabicyclo[5.4.0]undec-7-ene (710 mL, 4.75 mmol, 3.4 equiv) in anhydrous dimethyl sulfoxide (25 mL) was heated to 75° C. for 18 hours. The reaction mixture was cooled to room temperature and poured into distilled water adjusted to pH=7.4 with saturated aqueous sodium bicarbonate. The aqueous phase was extracted several times with chloroform. The chloroform layer was then extracted with 1N HCl and the acidic aqueous phase was back extracted with chloroform. The aqueous layer was adjusted to pH=7.4 with saturated aqueous sodium bicarbonate and extracted with chloroform. The chloroform extracts were dried over sodium sulfate, filtered and concentrated in vacuo to a dark oil which was purified by flash chromatography (chloroform/methanol 10:1 v/v) to give 65 mg, 12% yield of a white solid, m.p. 190°–212° C with decomposition.

Anal.: Calcd. for $C_{20}H_{22}FN_3O_4 \cdot 0.5H_2O$: C, 60.60; H, 5.80; N, 10.60. Found: C, 60.57; H, 5.70; N, 10.59.

I claim:

1. A compound of the formula wherein Q is methyl, Y is cyclopropyl and R is hydrogen, or a pharmaceutically acceptable salt or hydrate of said compound.

2. A pharmaceutical composition for treating or preventing a bacterial disease in a mammal comprising an antibacterially effective amount of a compound according to claim 1 and a pharmaceutically acceptable carrier.

3. A method of treating or preventing a bacterial disease in a mammal, said method comprising administering to said mammal an antibacterially effective amount of a compound according to claim 1.

* * * * *